(12) United States Patent
Brütsch et al.

(10) Patent No.: US 11,299,704 B2
(45) Date of Patent: Apr. 12, 2022

(54) MIXING DEVICE FOR MIXING THE CONTENT OF A BIOREACTOR, COMPRISING A SYNCHRONIZATION MECHANISM

(71) Applicant: SARTORIUS STEDIM BIOTECH GMBH, Göttingen (DE)

(72) Inventors: Simon Brütsch, Dübendorf (CH); Jochen Scholz, Göttingen (DE)

(73) Assignee: SARTORIUS STEDIM BIOTECH GMBH, Göttingen (DE)

( * ) Notice: Subject to any disclaimer, the term of this patent is extended or adjusted under 35 U.S.C. 154(b) by 28 days.

(21) Appl. No.: 15/776,604

(22) PCT Filed: Nov. 16, 2016

(86) PCT No.: PCT/EP2016/077880
§ 371 (c)(1),
(2) Date: May 16, 2018

(87) PCT Pub. No.: WO2017/085136
PCT Pub. Date: May 26, 2017

(65) Prior Publication Data
US 2018/0327707 A1 Nov. 15, 2018
US 2019/0390154 A2 Dec. 26, 2019

(30) Foreign Application Priority Data

Nov. 16, 2015 (DE) .......................... 102015119756.1

(51) Int. Cl.
*C12M 3/00* (2006.01)
*C12M 1/00* (2006.01)
(Continued)

(52) U.S. Cl.
CPC ............ *C12M 41/48* (2013.01); *C12M 27/16* (2013.01); *C12M 41/00* (2013.01); *G08C 25/00* (2013.01)

(58) Field of Classification Search
CPC ....... C12M 41/00; C12M 41/48; C12M 27/16
See application file for complete search history.

(56) References Cited

U.S. PATENT DOCUMENTS 4,293,643 A * 10/1981 Ohtake .................... B01F 9/002
366/142
5,164,796 A 11/1992 Di Guiseppi et al.
(Continued)

FOREIGN PATENT DOCUMENTS

CH 697035 A5 3/2008
DE 3248543 A1 7/1983
(Continued)

OTHER PUBLICATIONS

International Preliminary Report on Patentability dated May 22, 2018 by the International Searching Authority for Patent Application No. PCT/EP2016/077880, which was filed Nov. 16, 2016 and published as WO 2017/085136 dated May 26, 2017 (Inventor-Brütsch et al.; Applicant-Sartorius Stedim Biotech GmbH) (Translation Only-11 pages).

(Continued)

*Primary Examiner* — Nathan A Bowers
(74) *Attorney, Agent, or Firm* — Ballard Spahr LLP

(57) ABSTRACT

The present invention relates to a system comprising a mixing device for mixing the content of a bioreactor. The system is comprising at least one movement device for initiating a mixing movement in the bioreactor or in a holder for receiving a bioreactor and at least one sensor that can be arranged in or on the bioreactor for receiving at least one physiological or physical measurement variable. The mixing device or the bioreactor further comprises a sensor or (Continued)

Figure 1:
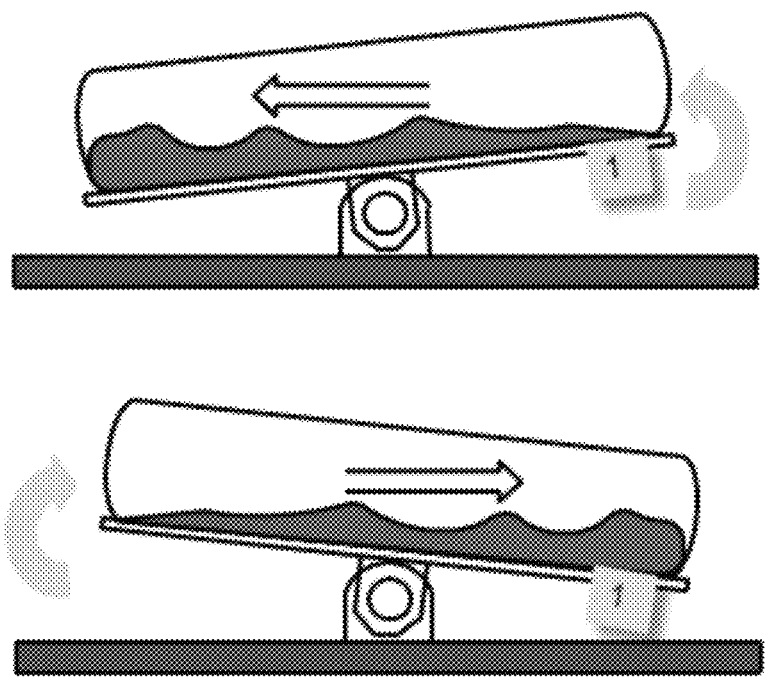

transmitter for generating a synchronization measurement variable.

12 Claims, 5 Drawing Sheets

(51) Int. Cl.
*C12M 1/36* (2006.01)
*C12M 3/06* (2006.01)
*C12M 1/34* (2006.01)
*G08C 25/00* (2006.01)

(56) References Cited

U.S. PATENT DOCUMENTS

| | | | |
|---|---|---|---|
| 6,730,471 | B1 | 5/2004 | Katerkamp et al. |
| 8,304,231 | B2 | 11/2012 | Röll |
| 2005/0153425 | A1* | 7/2005 | Xu .......................... C12M 25/08 435/287.1 |
| 2012/0097557 | A1 | 4/2012 | Baumfalk et al. |
| 2012/0244608 | A1* | 9/2012 | Selker ..................... C12M 27/16 435/288.7 |
| 2015/0093829 | A1* | 4/2015 | Swanda ................. C12M 23/26 435/420 |
| 2017/0036181 | A1 | 2/2017 | Boettcher et al. |
| 2017/0130186 | A1* | 5/2017 | Berry ...................... C12M 41/48 |

FOREIGN PATENT DOCUMENTS

| | | |
|---|---|---|
| DE | 102004039463 A1 | 2/2006 |
| DE | 102009037345 A1 | 12/2010 |
| DE | 102009055406 B3 | 5/2011 |
| DE | 102011017781 A1 | 10/2012 |
| DE | 102014105472 A1 | 10/2015 |
| EP | 0810281 A2 | 12/1997 |
| EP | 1778828 A1 | 5/2007 |
| JP | 2005-261230 A | 9/2005 |
| WO | WO-93/15402 A1 | 8/1993 |
| WO | WO-00/66706 A1 | 11/2000 |

OTHER PUBLICATIONS

International Search Report dated Feb. 6, 2017 by the International Searching Authority for Patent Application No. PCT/EP2016/077880, which was filed Nov. 16, 2016 and published as WO 2017/085136 dated May 26, 2017 (Inventor-Brütsch et al.; Applicant-Sartorius Stedim Biotech GmbH) (Original-4 pages; Translation-3 pages).

* cited by examiner

MIXING DEVICE FOR MIXING THE CONTENT OF A BIOREACTOR, COMPRISING A SYNCHRONIZATION MECHANISM

CROSS REFERENCE TO RELATED PATENT APPLICATIONS

This application claims the benefit of priority under 35 U.S.C. § 371 of International Application No. PCT/EP2016/077880, filed on Nov. 16, 2016, which claims the benefit of priority to European Application No. 1021015119756.1, filed on Nov. 16, 2015. The content of these earlier filed applications is hereby incorporated by reference.

The present invention relates to a mixing device for mixing of a bioreactor according to the preamble of the independent claim, as well as a process of mixing a bioreactor.

For production of culture media for microorganisms or cell cultures, or for controlled biotechnological processes such as cultivation of cells, the mixing or circulating of the bioreactor plays a particularly important role. Due to the different starting concentrations of substances and the metabolism of microorganisms and cells, respectively, during cultivation, there are local changes in concentrations of various chemical components in the media preparation or of nutrients, oxygen and the generated metabolites during cultivation. In order to allow for the same or at least controlled concentration conditions throughout the entire bioreactor, it is required to mix or circulate the fluid or suspension in the container during the entire process.

The use of flexible single-use bioreactors made of plastic foil plays a steadily growing role as compared to rigid containers composed of glass or stainless steel, in particular with regard to the continuously growing requirements for sterility of processes in biotechnology. In addition to their good suitability for sterilization, foil bags offer further advantages such as cost-efficient production, simple and space-saving storage, safety against contamination, and they make tedious purification after usage dispensable.

Devices for mixing of such bioreactors are also known as rockers, platform shakers, wobbling mixers, rotation shakers, vibration shakers, horizontal shakers, orbital shakers, and are described, for example, in patent applications DE3248543A1, CH697035A5 or EP1778828B1.

Such stirring devices are distributed, for example, by the company Sartorius under the brand name BIOSTAT® RM. With this device, the entire bioreactor is moved in such a way that the movement leads to mixing of the reactor content.

These devices are often comprising sensors for surveillance and control of the cultivation processes. These can be arranged inside and outside of the bioreactors.

It may occur that the sensor signal is compromised by the fluctuating fluid level inside of the bioreactor, which can lead to high signal fluctuations or erroneous measurements.

Such a disturbance can be induced, for example, by the sensor signal of a sensor which is arranged inside the bioreactor being influenced by the temporally varying fluid level. The sensor can be temporarily exposed and temporarily covered by liquid, or the fluid column above the sensor can be subject to fluctuations in height.

This is the case, e.g., for impedance sensors, by use of which, for example, the biomass of living cells in a culture broth can be determined.

This also occurs, for example, with conductivity sensors, by use of which the conductivity and thus a measure for dissolved substances in a cell suspension can be determined.

In both cases a reproducible result of the measurement can only be obtained when said sensors are ideally permanently covered by the same height of liquid column, or at least covered by a minimum liquid column, respectively.

It is therefore an object of the present invention to provide a mixing device for mixing of a bioreactor, as well as a process of mixing a bioreactor, which do not feature the disadvantages set forth above.

It is another object of the present invention to provide a mixing device for mixing of a bioreactor, as well as a process of mixing a bioreactor, which allow for a reproducible surveillance and control of the cultivation process.

These and other objects are solved by the processes and devices, respectively, set forth in the independent claims of the present invention. The dependent claims are describing preferred embodiments. Value ranges which are limited by numerical values are always meant to encompass said limiting numerical values.

SUMMARY OF THE INVENTION

Before the invention is described in detail, it is to be understood that this invention is not limited to particular components of said devices, or of said described process steps, as these processes and devices, respectively, may vary. It is further to be understood that the terminology is used herein only for the purpose of particular described embodiments, and is not intended to be limiting on purpose.

It must be noted that, as used in the specification and the appended claims, the singular forms "a," "an", and "the" include singular and/or plural referents unless the context clearly dictates otherwise. It is moreover to be understood that, in case parameter ranges are given which are delimited by numeric values, the ranges are deemed to include these limiting values.

According to the present invention, a system is provided comprising a mixing device for mixing of a bioreactor, comprising at least one movement mechanism for inducing a mixing motion in the bioreactor or in a holder of a bioreactor, at least one sensor attached to or in the bioreactor for monitoring at least one physiological or physical readout, wherein the mixing device or the bioreactor further comprise a sensor or transmitter for generating a synchronization readout.

Preferably it is provided that the system further comprises a synchronization mechanism for
 a) triggering the measurement of at least one physiological or physical readout on the basis of the synchronization readout and optionally the subsequent evaluation of at least one measured value, or
 b) selection of at least one monitored value of at least one physiological or physical readout on the basis of the synchronization readout, and optionally the subsequent evaluation of the at least one measured value, or
 c) setting-off the synchronization readout with the at least one physiological or physical readout.

Preferably it is further provided that the system comprises an evaluation device for displaying, recording and/or evaluating the at least one physiological or physical readout.

Such mixing devices are usually comprising a plate-shaped or tub-shaped holder for a single-use reactor, for example a bioreactor.

The bioreactors are being mounted on said holder, wherein they are fixed by use of clamps or hooks or other reversible fixing materials. The holder is being propelled and generates the mixing movement of the bioreactor's content. The holder hereby executes for example a rocking movement along a horizontal axis. The bioreactors can feature volumes of between 0.5 and 1000 liters.

Preferably it is provided that the synchronization readout is synchronized or synchronizable with the movement of the mixing device or the mixing movement in the bioreactor.

The term "synchronized" or "adapted to synchronization" ("synchronizable") as used herein encompasses in particular all such approaches wherein the synchronization readout is selected in such a way that the same picks up a clock pulse or rhythm of the mixing movement or a generated clock pulse or rhythm of an artefact generated directly or indirectly by the mixing movement.

In a preferred embodiment it is provided that the sensor for monitoring a physiological or physical readout and the sensor or transmitter for generating a synchronization readout are identical.

In such an embodiment, for example the physiological or physical readout can be discontinuously recorded, for example with a certain sampling frequency. By using an evaluation algorithm it can then be accomplished, e.g., that in cases when the physiological or physical readout exceeds or goes below a certain threshold value, the following or preceeding measured value is taken.

Such an embodiment can, e.g., be calibrated or taught in advance as the user experiments with various threshold values.

In another preferred embodiment it is provided that a sensor for monitoring of a physiological or physical readout and a sensor or transmitter for generating a synchronization readout are different from one another.

Preferably it is further provided that the sensor for monitoring of a physiological or physical readout is arranged for recording a time series of a physiological or physical readout.

Preferably it is further provided that the sensor or transmitter for generating a synchronization measured value is arranged for generating a time series of a synchronization measured value.

Preferably it is further provided that the bioreactor is mounted on a holder in which the mixing movement can be induced.

Preferably the system herein is designed in such a way that it can induce at least one of the mixing movements selected from the group consisting of
  a periodic movement
  a two-dimensional movement
  a three-dimensional movement
  a rocking movement along a horizontal axis and/or
  a rotational movement along a vertical axis.
in the bioreactor or in the holder of a bioreactor.

The frequencies of the mixing movements herein are preferably within a range between ≥5 and ≤200 min$^{-1}$ (i.e., ≥0.083 and ≤3.33 Hz). For a rocking movement the angle is preferably in a range between +/−3° and +/−15°.

Preferably it is further provided that the sensor for monitoring of at least one physiological or physical readout is selected from the group consisting of a
  capacitive sensor
  temperature sensor
  impedance sensor
  conductivity sensor
  sensor for measuring the optical density and/or turbidity
  sensor for measuring scattered light
  optical sensor for spectroscopy, especially absorption spectroscopy
  fluorescence sensor
  impedance spectroscopy sensor, and/or
  FTIR spectroscopy.

It is important herein that the data recording with regard to the physiological or physical readout can take different times depending on the sensor type, and that signal processing times of variable durations are required between successive measurements, respectively, which has an impact on the frequency of data recording that can be achieved.

Sensors which are amenable to a high frequency of read-out are particularly suited for a continuous or pseudo continuous data recording, respectively (i.e., with a high sampling frequency), whereas sensors which are only amenable to a low frequency of read-out are suited for a discontinuous data recording (i.e., for example, triggered by the synchronization readout).

Preferably it is further provided that the physiological or physical readout to be monitored is selected from the group consisting of
  biomass
  conductivity
  pH value
  temperature
  $pO_2$ and/or $pCO_2$
  optical density
  capacity
  cell parameter
  cell density
  cell diameter, and/or
  metabolite concentration.

These readouts individually or in combination allow for a statement on (i) the cultivation process (growth of the amount of cells, cell viability etc.), (ii) the quality of the cultivation conditions as well as the media and alike.

Preferably it is further provided that the sensor or transmitter for generating a synchronization readout is selected from the group consisting of a
  sensor or transmitter for monitoring of an angle position of the mixing device,
  sensor or transmitter for recording of data from an electronic, servo- or step motor or an electronic, servo- or step motor control,
  proximity sensor for monitoring the position of the bioreactor or its holder,
  sensor or transmitter for monitoring of the power consumption of an electronic, servo- or step motor,
  acceleration sensor for monitoring the momentary movement change of the bioreactor or its holder,
  filling-level meter for measuring of a fluid level in the bioreactor,
  pressure, load or weight sensor, and/or
  camera system/digital image processing.

Herein it also holds true that sensors which are amenable to a high frequency of read-out are suited for a continuous or pseudo continuous generation of the synchronization readout (i.e., with a high sampling frequency), whereas sensors which are only amenable to a low frequency of read-out are suited for a discontinuous generation of the synchronization readout (for example, by operating a switch or alike).

It is also important in this context that in the case of
  a) triggering the measurement of at least one physiological or physical readout on the basis of the synchronization readout, or b) selection of at least one recorded value of at least one physiological or physical readout on the basis of the synchronization readout, and optionally subsequent evaluation of the at least one value, respectively, optionally a time lag must be taken into account. In that sense, for example, the fluid present in the bioreactor will follow the induced mixing movement (e.g., a rocking movement) with a phase shift.

According to the present invention a transmitter creates a trigger signal or a digital signal (digital in the sense of on/off or high/low) for generating a synchronization readout. To this end, the transmitter can comprise, e.g., a switch which is for example operated always when the rocker or platform shaker is reaching its maximum deflection and is changing its direction of movement. At this moment of operating the switch, however, the wave in the culture fluid in the bioreactor that is induced by the movement has not yet reached the respective end of the vessel; this happens with a certain time lag. At this moment of operating the switch, therefore, a liquid column standing above a sensor positioned at the respective end of the vessel is not yet at its maximum—its maximum height is lagging behind the mixing movement with a phase shift.

Therefore it can make sense to take said phase shift into account with regard to triggering a measurement of at least one physiological or physical readout or the selection of at least one recorded value of at least one physiological or physical readout, respectively.

Preferably it is further provided that the synchronization mechanism is a component of the evaluation device.

Preferably it is furthermore provided that the bioreactor is a flexible single-use bioreactor made of a foil material.

The use of flexible single-use bioreactors made of plastic foil plays a steadily growing role as compared to rigid containers composed of glass or stainless steel, in particular with regard to the continuously growing requirements for sterility of processes in biotechnology. In addition to their good suitability for sterilization, foil bags offer further advantages such as cost-efficient production, simple and space-saving storage, best-possible safety against contamination, and they make tedious purification after usage dispensable.

Such flexible single-use bioreactors are being distributed for example by the company Sartorius under the trade name "CultiBags® RM" and "Flexsafe® RM". They are available for example in volumes of 2 L, 10 L, 20 L, 50 L, 100 L and 200 L.

According to the present invention, furthermore, a mixing device for mixing of a bioreactor is provided, wherein said mixing device is arranged for use in a system according to the description set forth above. The mixing device is comprising at least one movement mechanism for inducing a mixing movement in the bioreactor or in a holder of a bioreactor.

According to the present invention, furthermore a process is provided for mixing of a bioreactor, wherein by use of a movement mechanism a mixing motion in a bioreactor is induced, at least one physiological or physical readout is monitored by use of a sensor attached to or in the bioreactor, by use of an evaluation device the at least one physiological or physical readout is displayed, recorded and/or evaluated, a synchronization readout is generated by use of a sensor or transmitter for generation of a synchronization readout, and wherein by use of a synchronization device
  a) the measurement of at least one physiological or physical readout is triggered and the at least one measured value is optionally subsequently displayed, recorded and/or evaluated, or
  b) monitored values of at least one physiological or physical readout are selected on the basis of the synchronization readout, and optionally the measured values are subsequently evaluated, or
  c) the synchronization readout is set off with the at least one physiological or physical readout.

With regard to the device according to the present invention and the process according to the present invention, respectively, it has to be distinguished between continuously (or pseudo continuously in the case of digital data recording, respectively, i.e., sampled) and discontinuously monitored physiological or physical readouts and synchronization readouts.

For example, the synchronization readout can be recorded continuously or pseudo continuously. When a certain criterion is fulfilled, for example when a given threshold is exceeded or undercut, at zero crossing, with reaching a local maximum or local minimum, then measurement of a physiological or physical readout can be triggered. In this case the physiological or physical readout is being discontinuously recorded.

For example, the synchronization readout can be discontinuously recorded, for example by operating a switch at all times when the mixing device is moving through a certain position. These discontinuously recorded synchronization readout can then trigger measurement of a physiological or physical readout (discontinuous) or select in a continuously or pseudo continuously recorded physiological or physical readout certain values.

Quite as well can the discontinuously or continuously or pseudo continuously, respectively, recorded synchronization readout be set off with the discontinuously or continuously or pseudo continuously, respectively, recorded physiological or physical readout.

According to the present invention it is further provided a process for determination of at least one optimal time point of measurement or time period of measurement for the recording of at least one physiological or physical readout by use of a sensor positioned in or at a bioreactor, wherein by use of a mixing device a mixing movement is induced in the bioreactor, wherein by use of a sensor or transmitter a synchronization readout is generated, and wherein by use of a synchronization device
  a) the measurement of at least one physiological or physical readout is triggered and at least one measured value is optionally subsequently displayed, recorded and/or evaluated, or
  b) the synchronization readout is set off with the at least one physiological or physical readout, or
  c) monitored values of the at least one physiological or physical readout are selected on the basis of the synchronization readout, and optionally the measured values are subsequently evaluated, or
  d) at least one physiological or physical readout are recorded on the basis of the synchronization readout, selected in dependence from the synchronization readout according to a predetermined rule and subsequently used as specification for further recording of the at least one physiological or physical readout.

Preferably the mixing movement herein is at least one selected from the group comprising
  a periodic movement
  a two-dimensional movement
  a three-dimensional movement
  a rocking movement along a horizontal axis, and/or a rotational movement along a vertical axis.

In a particularly preferred embodiment of the present invention it is provided that a frequency spectrum is gone through for recording of the physiological or physical readout and/or the physiological or physical readout of a frequency spectrum consists.

Some measure processes are using a modulated readout which is dynamically modified in its frequency. In the process a frequency spectrum is gone through for each measurement (a so-called sweep). This method is used with many spectroscopic processes, for example, in impedance spectroscopy as well as optical spectroscopy procedures such as UV-, IR, or Raman spectroscopy and FTIR. Especially physiological or physical readouts generated that way usually need to be discontinuously recorded.

In doing so it may happen that the selection frequency concerning the physiological or physical readout is lower than or in a comparable range as the frequency of the mixing movement. In other words: the time period required for running through the frequency spectrum ("sweep period") cannot be neglected against the change of the fluid level in the reactor.

Particularly preferably it is provided that the frequency spectrum is discretely and discontinuously recorded in dependency of the synchronization readout.

That way it can be ensured that the different frequencies or wave lengths of the spectrum, respectively, are each measured at a time point when the fluid level at the measure position is identical, so that a spectrum can be recorded that is reproducible and not influenced by fluid fluctuations.

According to the present invention, furthermore, a system or a device is provided according to the description above for use in a process as described above.

According to the present invention, furthermore, the use of a system, a device or a process according to the description above is provided for cultivation of microorganisms and/or cells.

This concerns in particular the cultivation of mammalian cells, plant cells, insect cells, stem cells and microorganisms.

The cultivation of said microorganisms and/or cells is preferably performed for amplifying the same and/or for production of biomolecules, such as proteins, in particular for industrial or pharmaceutical purposes.

Said proteins can be, for example, antibodies, hormones, enzymes, growth factors, cytokines and the like.

Furthermore, according to the present invention, a process for teaching or calibrating a system as described above is provided, wherein in a test run a threshold value concerning (a) the physiological or physical readout or (b) the synchronization readout is defined or determined, that, when it is exceeded or underrun, triggers selection of a measured value of the physiological or physical readout that stands in a timely connection with said exceeding or underrun of the threshold value.

By this process, the best-suited measure time point is thus determined in an upstream procedure.

DRAWINGS AND EXAMPLES

The present invention is further described by the drawings and examples shown and discussed in the following. It is to be understood that the drawings and examples are for illustration purposes only and are not intended to limit the scope of the invention in any way.

FIG. 1 depicts a bioreactor on a rocking shaker according to the above description with a sensor 1 for reception of a physiological or physical readout. It can be seen that depending on the mixing movement there is temporarily a high and temporarily a low fluid column standing over the sensor which can compromise the measure result of sensor 1.

Figure 2:
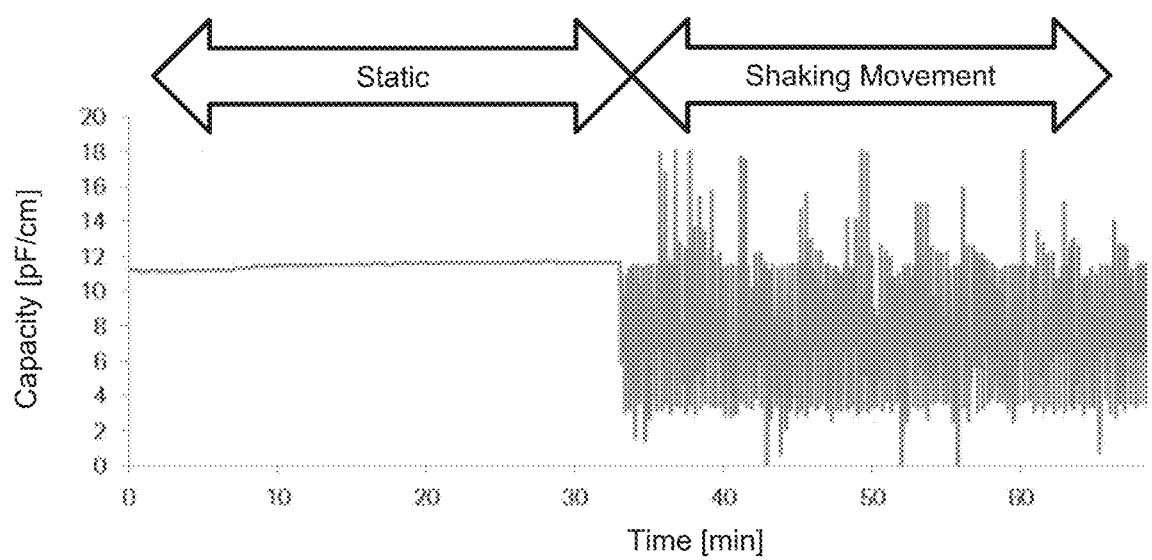

FIG. 2 depicts a time course of a capacity measurement using a four-electrodes sensor in a bioreactor. During the first 35 seconds the bioreactor is resting, whereas starting from the 35th second a mixing movement is induced in the bioreactor. The wave movement thereby generated is impairing the measure signal significantly.

Figure 3A:
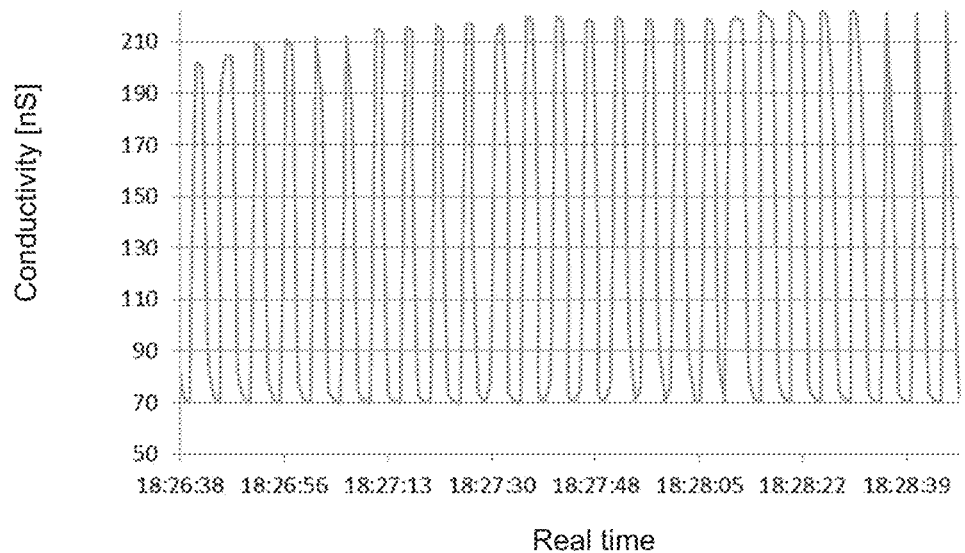

FIG. 3a depicts a physiological readout, in this case conductivity, from a bioreactor which is shaken on a mixing device according to the present invention by a tilting movement along a horizontal axis with a frequency of 12 bpm. Due to the wave movement the fluid column above the conductivity sensor is fluctuating, significantly influencing the measure signal. The conductivity sensor picks up the conductivity between the measuring electrodes on the sensor surface. Only with full coverage and a sufficient fluid level above the sensor the measure signal thus corresponds to the actual conductivity of the fluid in the sense of a physiological parameter or material property which in turn allows for conclusions on the concentration of a dissolved substance in the solution. In FIG. 3a, only the values at the maxima are representing actual conductivity as a characteristic feature of the fluid in the bioreactor.

Figure 3B:
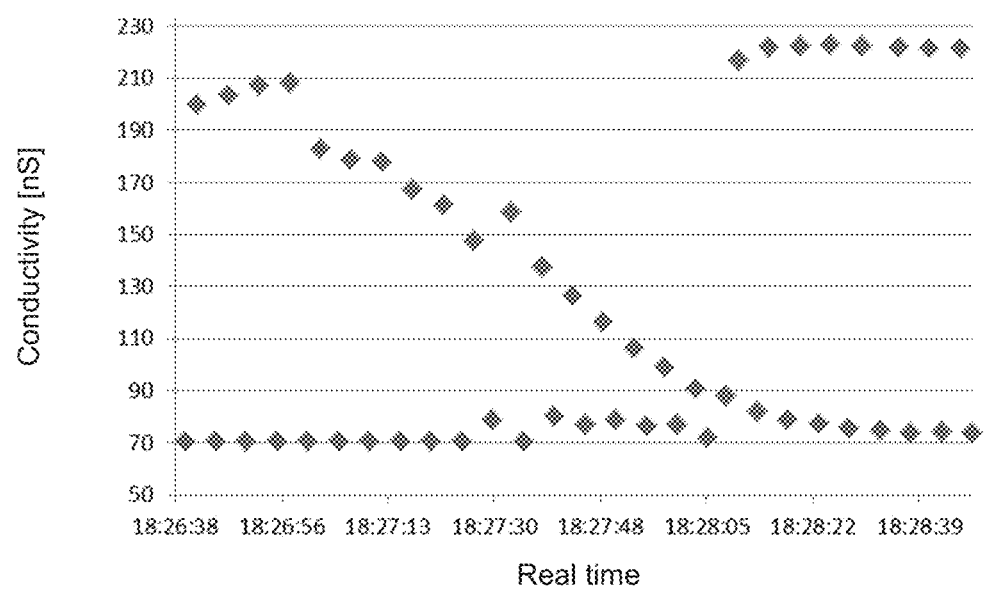
Figure 3C:
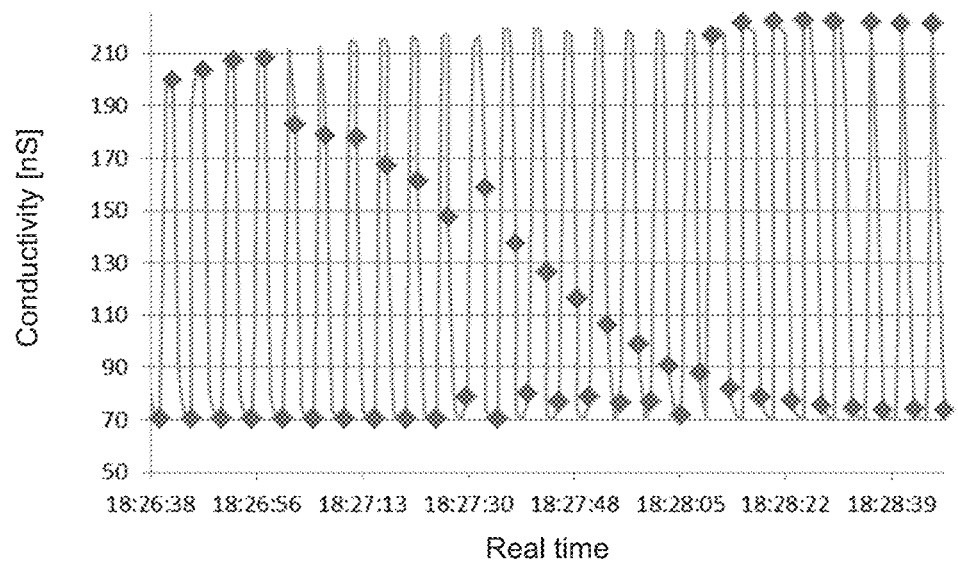

If a slower conductivity detector is used in this system, which for example provides measure values only every three seconds, measure signals are derived as shown by the data points of the data series in FIG. 3b: Partially the maxima and minima of the conductivity at the location of measurement modulated by the fluid movement are still met. But due to overlapping frequency fluctuations, many measure points also migrate to the shoulders. In this measurement situation it is extremely difficult to determine the momentary maximum value of conductivity at the sensor, i.e., the conductivity of the fluid as a physiological parameter. This becomes clear with the superposition of actual conductivity (solid line) with the sensor signal of the slower sensor (measure points) in FIG. 3c.

Figure 3D:
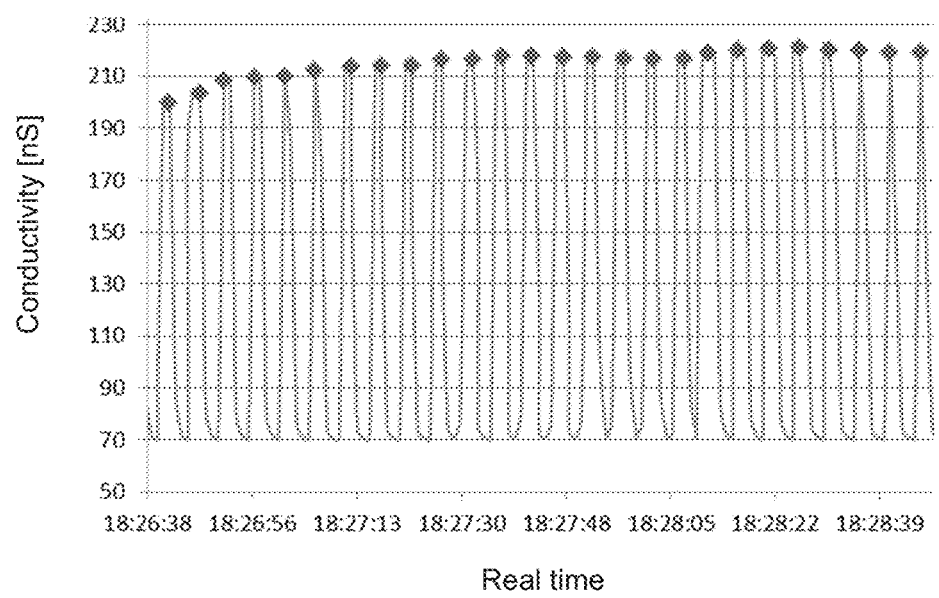

However, if the slow sensor, which takes at least three seconds between two measurements, thus having a maximum frequency of measurements of 0.333 Hz, is synchronized with the wave movement, the measurement can always be triggered at the relevant time point of maximal sensor coverage. This situation is depicted in FIG. 3d with the measure points—here again for comparison in superposition with the actual modulated conductivity at the position of measurement (solid curve). The slow sensor measures in this case only with ca. 0.2 Hz, but because of the synchronization with the wave movement in the bioreactor always at the relevant time point, wherein synchronization occurs for example by use of a fluid level sensor. The sensor does herein not necessarily measure with a fixed frequency, because the wave movement is partially chaotic and the synchronization readout thus corresponds only on the average to the periodicity of the moving mixing device.

Figure 3E:
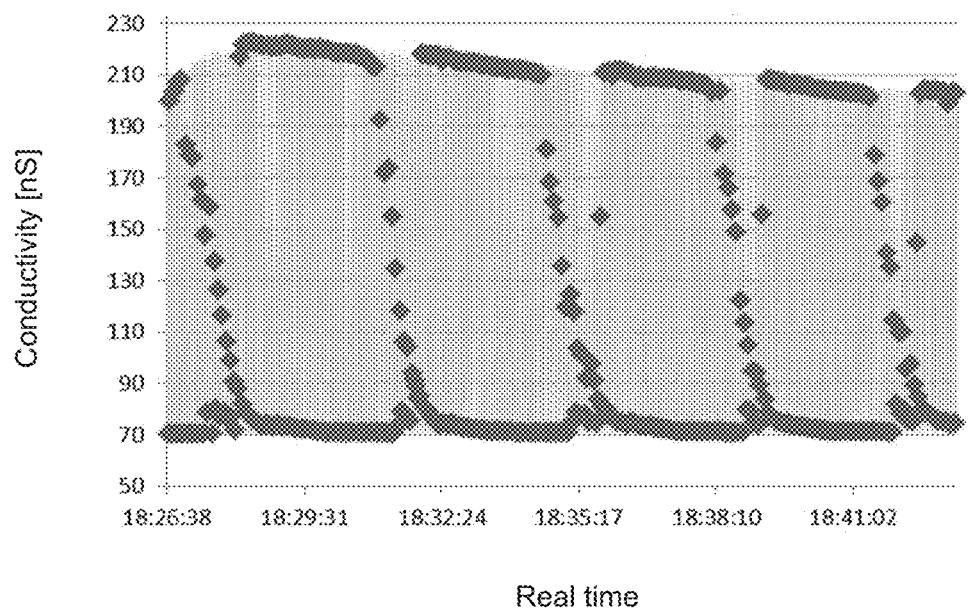
Figure 3F:
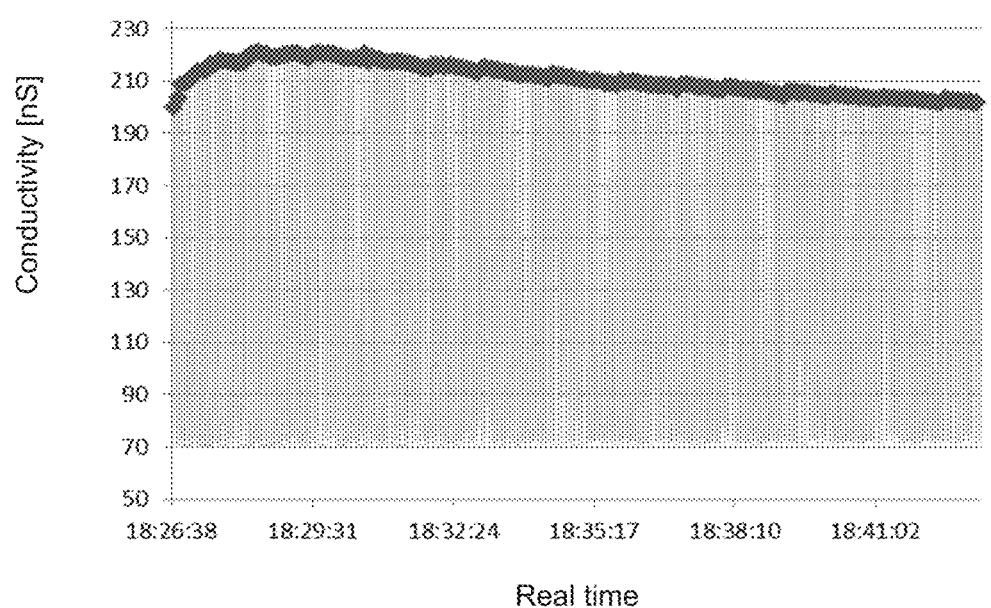

The advantage of synchronization is particularly visible if the physiological readout, i.e., the conductivity, is changing over time and the changes are occurring in similar time periods as the overlapping frequency fluctuations between slow sensor detection and mixing movement. Such an example is summarized in FIGS. 3e and 3f Solid curves are again showing the respective momentary conductivity at the sensor position. It is heavily modulated due to the fluctuating fluid level above the sensor caused by the mixing movement and corresponds only at maximal values to the conductivity of the fluid to be measured as physiological parameter. In the example in FIGS. 3e and 3f the conductivity of the fluid is first increasing over a time period of ca. two minutes from 195 nS to 225 nS and then again declines over a time period of ca. 12 minutes. In FIG. 3e the respective measure signal of a slow sensor with a frequency of measurement of 0.333 Hz is depicted again with the measure points. Especially the course of the signal increase over two minutes could not be reconstructed from this measure signal. FIG. 3f in contrast depicts the measurement result of a synchronized slow detector (measure points) superimposed with the actual momentary conductivity. As synchronization readout a fluid level signal serves here again for example. In FIG. 3f the entire act of dynamic change of the physiological readout can thus be followed, as the slow synchronized sensor always measures at the relevant time point of maximal sensor coverage.

What is claimed is:

1. A system comprising a mixing device for mixing of a bioreactor and a synchronization device,
   the mixing device comprising:
   at least one movement device for inducing a mixing motion to the bioreactor or to a holder of the bioreactor,
   at least one sensor attached to or in the bioreactor for recording at least one physiological or physical parameter,
   wherein the mixing device or the bioreactor further comprises a sensor for generating a synchronization readout, namely a trigger signal or a digital signal (on/off or high/low),
   wherein the synchronization readout is synchronized or synchronizable with the mixing motion induced to the bioreactor or to the holder thereof,
   wherein the synchronization device:
   a) triggers the measurement of at least one physiological or physical parameter on the basis of the synchronization readout or
   b) selects at least one recorded value of at least one physiological or physical parameter on the basis of the synchronization readout; and
   wherein the system uses a frequency spectrum for calculating and/or recording the physiological or physical parameter and/or physiological or physical parameter consists of a frequency spectrum, wherein the frequency spectrum is discretely and discontinuously recorded in dependency of the synchronization readout.

2. The system of claim 1, further comprising an evaluation device for displaying, recording and/or evaluating the at least one physiological or physical parameter.

3. The system of claim 1, wherein a sensor for recording a physiological or physical parameter and a sensor or transmitter for generating a synchronization readout are different from one another.

4. The system of claim 1, wherein the sensor for recording at least one physiological or physical parameter is selected from the group consisting of a capacitive sensor, an impedance sensor, a conductivity sensor, a sensor for measuring the optical density and/or turbidity, a sensor for measuring scattered light, an optical sensor for spectroscopy or absorption spectroscopy, a fluorescence sensor, an impedance spectroscopy sensor and a FTIR spectroscopy sensor.

5. The system of claim 1, wherein the physiological or physical parameter to be recorded is selected from the group consisting of biomass, conductivity, pH value, temperature, $pO_2$ and/or $pCO_2$, optical density, capacity, cell parameter, cell density, cell diameter, and a metabolite concentration.

6. The system of claim 1, wherein the sensor for generating the synchronization readout is selected from the group consisting of a sensor for recording of an angle position of the mixing device, sensor for recording of data from an electronic, servo- or step motor or an electronic, servo- or step motor control, proximity sensor for monitoring the position of the bioreactor or its holder, sensor for recording of the power consumption of an electronic, servo- or step motor, acceleration sensor for recording the momentary movement change of the bioreactor or its holder, filling-level meter for measuring of a fluid level in the bioreactor, pressure, load or weight sensor, and camera system/digital image processing.

7. The system of claim 2, wherein the synchronization device is a component of the evaluation device.

8. The system of claim 1, wherein the frequency spectrum is generated using one or more spectroscopic processes, wherein the one or more spectroscopic processes are impedance spectroscopy or optical spectroscopy.

9. The system of claim 8, wherein the optical spectroscopy is UV, IR, Raman or FTIR spectroscopy.

10. A method for mixing a bioreactor using the system of claim 1.

11. A method for teaching or calibrating the system of claim 1, the method comprising performing a test run to determine a threshold value concerning the physiological or physical parameter or the synchronization readout, wherein the synchronization readout is defined or determined, when it is exceeded or underrun, thereby triggering selection of a measured value of the physiological or physical parameter that stands in a timely connection with said exceeding or underrun of the threshold value.

12. The method of claim 11, wherein the synchronization device computes a synchronization variable with the at least one physiological or physical measurement variable.

* * * * *